(12) United States Patent
Capitaine et al.

(10) Patent No.: US 8,025,653 B2
(45) Date of Patent: Sep. 27, 2011

(54) LUER CONNECTOR, MEDICAL CONNECTOR AND TRANSFER SET COMPRISING SUCH A CONNECTOR

(75) Inventors: François Capitaine, Anglet (FR); François Durand, Bayonne (FR)

(73) Assignee: Technoflex, Bidart (FR)

( * ) Notice: Subject to any disclaimer, the term of this patent is extended or adjusted under 35 U.S.C. 154(b) by 1318 days.

(21) Appl. No.: 11/410,156

(22) Filed: Apr. 25, 2006

(65) Prior Publication Data

US 2007/0244447 A1 Oct. 18, 2007

(30) Foreign Application Priority Data

Mar. 24, 2006 (FR) ...................................... 06 51030

(51) Int. Cl.
*A61M 5/32* (2006.01)
*A61M 5/14* (2006.01)
(52) U.S. Cl. ........................................ 604/411; 604/256
(58) Field of Classification Search .................. 604/246, 604/256, 533, 534, 535, 537, 539, 403
See application file for complete search history.

(56) References Cited

U.S. PATENT DOCUMENTS

| 4,346,703 | A | * | 8/1982 | Dennehey et al. ............. 604/406 |
| 5,171,234 | A | * | 12/1992 | Jepson et al. .................. 604/534 |
| 5,429,619 | A | * | 7/1995 | Furnish .......................... 604/537 |
| 5,454,409 | A | * | 10/1995 | McAffer et al. ............... 141/329 |
| 5,676,346 | A | * | 10/1997 | Leinsing .................... 251/149.1 |
| 5,749,861 | A | * | 5/1998 | Guala et al. .................... 604/249 |
| 5,833,213 | A | * | 11/1998 | Ryan ........................... 251/149.1 |
| 6,364,143 | B1 | * | 4/2002 | Knierbein ....................... 215/247 |
| 6,485,479 | B1 | * | 11/2002 | Knierbein ....................... 604/411 |
| 6,610,040 | B1 | * | 8/2003 | Fowles et al. ................. 604/413 |
| 6,709,424 | B1 | * | 3/2004 | Knierbein ....................... 604/411 |
| 7,516,846 | B2 | * | 4/2009 | Hansen ........................... 206/528 |
| 2004/0039365 | A1 | * | 2/2004 | Aramata et al. ............... 604/411 |
| 2004/0116891 | A1 | * | 6/2004 | Curutcharry .................. 604/403 |
| 2008/0177244 | A1 | * | 7/2008 | Capitaine et al. ............. 604/414 |

FOREIGN PATENT DOCUMENTS

| DE | 101 46 007 | | 10/2002 |
| EP | 0 499 481 | | 2/1992 |
| EP | 1 378 223 | | 1/2004 |
| EP | 1837005 | A1 * | 9/2007 |
| WO | WO 98/48765 | | 11/1998 |
| WO | WO 02/056946 | | 7/2002 |
| WO | WO 03/077826 | | 9/2003 |
| WO | WO 2004/091472 | | 10/2004 |
| WO | WO 2006005391 | A1 * | 1/2006 |

\* cited by examiner

*Primary Examiner* — Nicholas D Lucchesi
*Assistant Examiner* — Aarti B Berdichevsky
(74) *Attorney, Agent, or Firm* — Young & Thompson

(57) ABSTRACT

A luer connector, a medical connector for a receptacle having a pierceable stopper and a transfer set including such a luer connector. This luer connector comprises an internal conduit (11) for a fluid to pass, elements (8) of connection to a second luer connector (16) having a perforator (21), these connection elements (8) being placed at one of its ends. This end also includes a continuous rim (24) forming a projection in the conduit (11) so as to provide a seal thereon when the perforator (21) is introduced into the conduit with a view to coupling these connectors (7, 16). A breakable membrane (10) is also placed in the conduit (1*i*) so as to be separated when the second luer connector (16) is coupled to this luer connector.

10 Claims, 3 Drawing Sheets

LUER CONNECTOR, MEDICAL CONNECTOR AND TRANSFER SET COMPRISING SUCH A CONNECTOR

The present invention concerns a luer connector, a medical connector and a transfer set comprising such a luer connector or medical connector for the administration of liquid substances for medical purposes.

This transfer set is in particular intended for reconstituting an active principle, such as a medicinal powder for the treatment of cancer, contained in a bottle, from a liquid constituent.

The reconstitution is generally carried out by an operator before administration of the medication to the patient. This reconstitution is obtained, by way of example, by introducing, into the bottle containing the active principle, a solution to be diluted contained in a receptacle such as a flexible pouch or bottle.

In order to avoid any human errors during such manipulation, use is generally made of reconstitution sets consisting in particular of a connector intended to be fixed to the bottle containing the active principle.

This connector can comprise a bell enabling it to be fixed to the neck of a bottle by clipping, the bell then enclosing at least a portion of it.

However, this connector of the prior art is particularly complex since typically it consists of an assembly of various parts fitting in one another.

It is then found that, whatever the care given to the formation of the connector, there exist, between these various parts, spaces liable to trap quantities of fluid containing the active principle that it is sought to administer to the patient.

In addition, the connectors of the prior art are generally large in size. Consequently these losses may be further increased by the presence of large contact surfaces between the connector and the fluid containing the active principle, which are liable to retain a certain quantity of this fluid.

These reconstitution devices do not therefore allow optimum transfer of the fluid containing the active principle after reconstitution.

However, medicinal powders for cancer treatment have a very high cost. They are in addition predosed in order to correspond exactly to the dose required for a particular treatment phase for the patient.

Such losses may give rise to insufficient administration of the treatment to the patient with the consequences that may stem from this on the state of health of the said patient. What may be possibly prove to be more serious, depending on the pathology, is that the patient may receive doses which are variable from one phase of treatment to another.

Moreover, these connectors cannot fit on any existing bottle. They are intended to be connected to bottles having predetermined shapes since the bell at least partially covers the body of the bottle. It is therefore necessary to have available a set of connectors for making connections with different bottles.

These connectors of the prior art also make it possible to achieve preconnections without communication in order to package connector/bottle assemblies ready for use. These assemblies thus produced can then be stored with a view to subsequent use.

However, it is found that it is difficult to check, before use, the state of these connectors in order to check whether the sterility of the assembly used is still intact.

It is also known that piercing the stopper of a bottle contacting an active principle, such as a powder, generates a slight suction of the air external to the bottle through the connector. This suction may, with the connectors of the prior art, give rise to contamination of the content of the bottle.

Likewise, the coupling of a male luer connector and a female luer connector as obtained by screwing a ferrule onto a thread requires particular attention on the part of the operator whilst it is being done in order to ensure impermeability of this connection.

The operator must in particular check that there is complete screwing of the ferrule of the first connector onto the thread of the other connector. An error in manipulation, for example insufficient screwing, may result in contamination of the bottle, It would therefore be advantageous to reinforce the security of the connector in order to prevent the content of the bottle possibly being able to be exposed to contaminants when it is connected by an operator to the connection element of a solute pouch.

There is also known a transfer set for administering a mixture of liquids for medical purposes from the present applicant (WO 02/056946). This mixing of liquids is in particular obtained from a so-called main flexible pouch containing a first liquid and at least one auxiliary flexible pouch containing a second liquid, able to be connected to the main pouch by means of a pair of connectors of the luer type, respectively male and female.

Each of these connectors comprises, at one end, a breakable section engaged in the end of a tube connected to one of the pouches and, at the other end, a means of coupling to the other connector, provided with means of locking in the coupled position of the said connectors.

This transfer set advantageously makes it possible to offer administration sets ready for use. This transfer set then comprises a main pouch, for example of diluent, preconnected, that is to say connected by a tubular connection but not communicating, to a dosed pouch or in parallel to several dosed pouches of active principles or nutrients, and where communication with the pouch of diluent can be achieved, in situ, at any time and instantaneously by breaking the breakable sections of the luers of the communication to be established.

This transfer set, which gives very satisfactory results, can nevertheless be improved in particular for its use with a bottle containing an active principle.

The luer connector intended to be connected to the bottle in fact requires the use of an adapted connector on the bottle for its assembly. The connector must have a tube at its end to allow the introduction of the end of a luer connector. The transfer set becoming complex, losses of active principle and/or contamination of the content of the bottle are consequently possible during reconstitution.

The present invention aims to mitigate these various drawbacks by proposing a luer connector and a medical connector comprising such a connector which are particularly simple in their design and operating method, compact, economical and making it possible to limit to the maximum the risk of contamination of the content of a receptacle when such connectors are installed.

Another objective of the present invention is to enable the operator to very easily check the integrity of an active substance contained in a preconnected connector/bottle assembly before it is connected to a solute pouch.

To this end, the invention concerns a luer connector having an internal conduit for a fluid to pass.

According to the invention, this luer connector comprises:
means of connection to a second luer connector having a perforator, these connection means being placed at one of its ends, this end also comprising a continuous rim forming a projection in the conduit so as to ensure the impermeability of this conduit when the perforator of the second luer connector is introduced into this conduit with a view to coupling these connectors, and a breakable membrane is placed in the conduit so as to be separated when the second luer connector is coupled to the luer connector.

The continuous rim constitutes a seal which, as soon as it is put in contact with the perforator of the second luer connector, forms a sealed connection between this rim and the external surface of the perforator.

Thus, when the perforator is introduced further into the conduit in order to achieve the coupling of the male and female connectors, the separation of the membrane does not give rise to the introduction of any air into the bottle other than that already contained in the conduit. The sealed connection forms a barrier to the passage of the external air into the bottle. The risks of any contamination of the content of the bottle are thus greatly minimised.

In the case of anticancer drugs, the products contained in the bottle cause emissions of gases. These are particularly toxic and can endanger the health of the user or of the patient if they are expelled from the bottle. The sealed connection of the invention therefore also makes it possible to guarantee that these gases remain confined and are not in contact with the user.

This seal is achieved by virtue of a precise assembly of the various parts of the invention and the connection between each of them is perfectly hermetic.

In various particular embodiments of this luer connector, each having its particular advantages and open to many possible technical combinations:

the membrane comprises one or more predetermined weakened zones for facilitating its separation, the membrane comprises a reinforcement zone on a portion of its periphery so that the said membrane remains secured to the internal conduit of the luer connector, the membrane is placed in the conduit so that the perforator of the second connector covers the portion or portions of the separated membrane after coupling of the connectors, Whether the membrane has been separated in a single piece from the conduit or in several portions by the perforator, this embodiment advantageously makes it possible to move this membrane away from the central fluid communication path as determined by the internal conduit of the luer connector. Obstruction of the conduit providing the fluid communication is prevented and thus any losses of active principle after constitution are minimised.

the connection means comprise a ferrule or external thread, it comprises a locking member intended to cooperate with a complementary locking member placed on the said second connector in order to lock the said luer connectors in position, This locking member preferably comprises means of the non-return catch type.

the end of the luer connector also comprises a breakable element.

The invention also relates to a medical connector for a receptacle comprising a pierceable stopper, this connector comprising a coupling element comprising an annular wall surrounding a piercing element.

According to the invention, the piercing element comprises an internal conduit in fluid communication with a tube portion, this tube portion being placed at least partially projecting from the coupling element, a luer connector as described previously is partially inserted in the tube portion, and the medical connector is in a single piece.

In various particular embodiments of this medical connector, each having its particular advantages and open to many possible technical combinations:

the luer connector not comprising any locking member, the medical connector comprises a locking member intended to cooperate with a complementary locking member placed on the second connector in order to lock these luer connectors in the coupled position, the locking member comprises means of the non-return catch type placed at the end of the tube portion, the tube portion having an inside diameter d, the luer connector comprises an internal conduit of diameter $d_1<d$.

The invention also concerns a transfer set for preparing a mixture for medical purposes.

According to the invention, this transfer set comprises a luer connector as described previously and a second luer connector comprising at one end a perforator and a complementary locking member for locking these luer connectors in the coupled position.

Finally, the invention relates to a transfer set for preparing a mixture for medical purposes.

According to the invention, this transfer set comprises a medical connector as described previously and a second luer connector comprising at one end a perforator and a complementary locking member intended to cooperate with the locking member of the said medical connector in order to lock this second luer connector and this medical connector in the coupled position.

This second luer connector preferably comprises at its end a breakable section intended to be engaged in the end of a tube.

This transfer set advantageously makes it possible to establish a preconnection between a bottle containing an active principle and a receptacle such as a solute pouch or a bottle, containing a liquid constituent.

This preconnection is carried out in a particularly secure manner because of the locking of the coupling of each pair of connectors, and prevents any cutaneous or airborne contact of the care staff with potentially very active substances.

The locked connection between the receptacle containing the liquid constituent and the bottle containing the active principle prevents any contamination also during the operations of disposing of the pouches after use, since the assembly is disposed of without separation of these elements thus assembled.

There is thus, through a simple, practical and rapid manipulation, the assurance of producing mixtures without loss of an active principle and a liquid constituent.

The invention will be described in more detail with reference to the accompanying drawings, in which.

Figure 1:
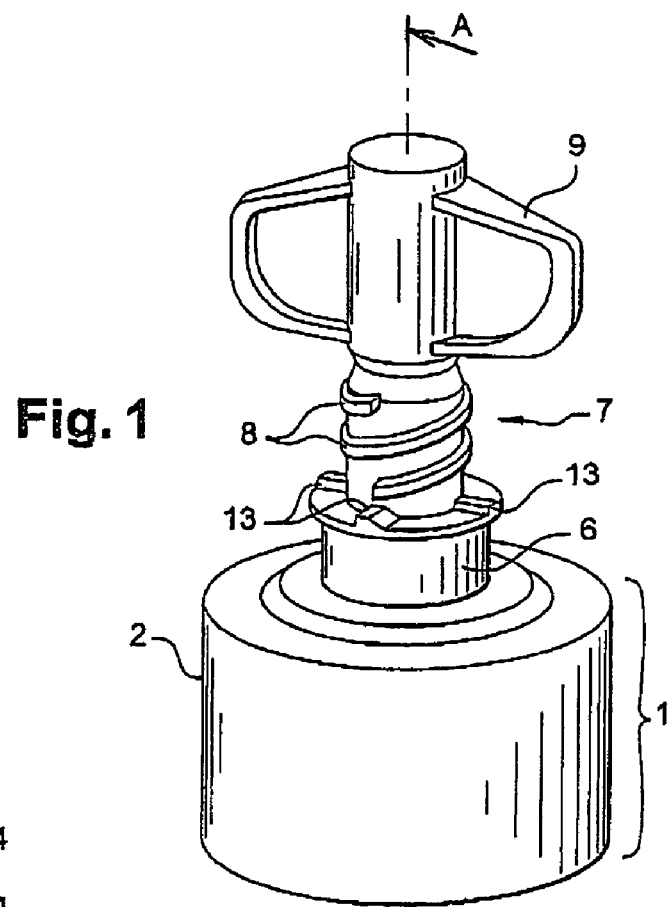
FIG. 1 is a schematic representation of a medical connector according to one embodiment of the invention.
Figure 2:
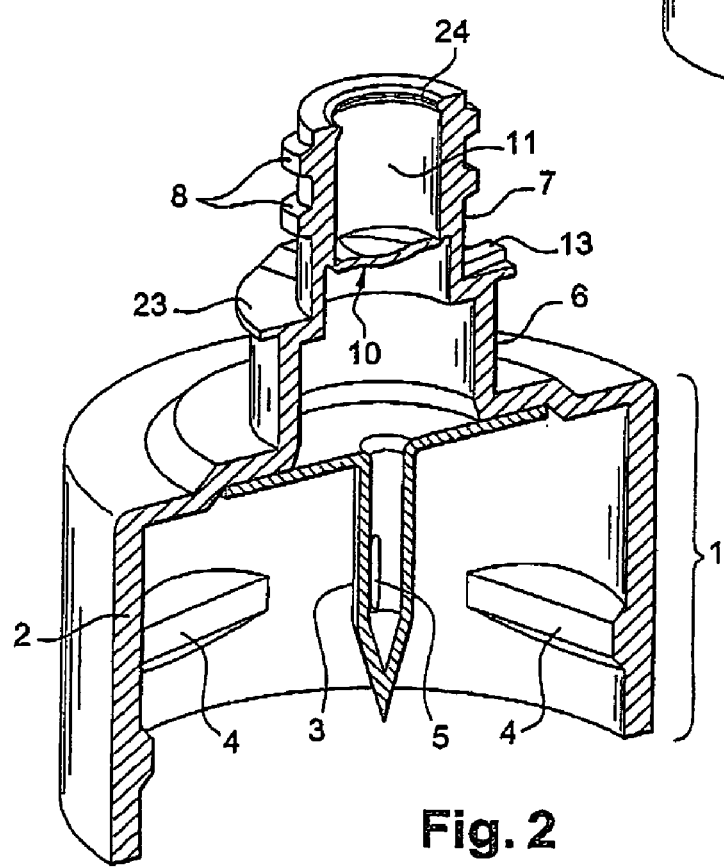
FIG. 2 is a view in section along the axis A-A of the connector of FIG. 1, the breakable element placed at the end of the female luer connector having been removed.

FIG. 1 shows a medical connector for a receptacle comprising a pierceable stopper according to a particular embodiment of the invention. This single-piece connector comprises a coupling element 1 comprising an annular wall 2 surrounding a piercing element 3 (FIG. 2).

The annular wall 2 comprises a fixing element 4 in its bottom part, which is intended to ensure the connection of the coupling element 1 with the end of the bottle to which the medical connector is intended to be connected. The height of the annular wall 2 is preferably less than 15 mm, which makes this medical connector adaptable to any type of bottle, whatever its shape.

This fixing element 4 is preferably a rim, continuous or not (FIG. 2), placed on the internal surface of the annular wall 2.

The piercing element 3, which is here a pointed protuberance (spike), comprises one or more orifices 5 at its end or close to it. These orifices 5 communicate with the internal conduit of the piercing element 3, which is in fluid communication with a tube portion 6 projecting from the coupling element 1. This tube portion 6 has an inside diameter d.

A female luer connector 7 is placed in line with this tube portion 6. The body of this female luer connector 7 is slightly inserted in the tube portion 6.

This female luer connector 7 has at its end opposite to the tube portion 6 an external thread 8 intended to cooperate, in a known manner, with a cylindrical ferrule for coupling a male luer connector of the transfer set.

A breakable element 9 is also fixed to this end of the female luer connector 7. This breakable element 9 is advantageously a quarter-turn stopper connected by a thin bridge to the end of the body of the female luer connector 7. This quarter-turn stopper can be disconnected from the end of the female luer connector by a simple manual rotation of a quarter of a turn.

This breakable element 9 has a dual role. It first of all enables the operator to very easily check, by a simple glance, the integrity of an active substance contained in a preconnected connector/bottle assembly.

However, it also forms a double protective barrier for the content of the bottle with a membrane 10 placed in the internal conduit 11 of the female luer connector 7.

Thus the internal conduit 11 is protected from any contamination as long as the quarter-turn stopper has not been broken and, at the same time, the content of the bottle is at no time exposed to the air since the membrane 10 is placed in the internal conduit so that it is broken only when a male luer connector is coupled to the female luer connector 7 in order to proceed with the reconstitution.

In addition, the end of the female luer connector comprises a continuous rim 24 forming a projection in the internal conduit 11 so as to ensure the impermeability of this conduit when the perforator of the male luer connector is introduced into the conduit with a view to coupling these connectors.

Figure 3:
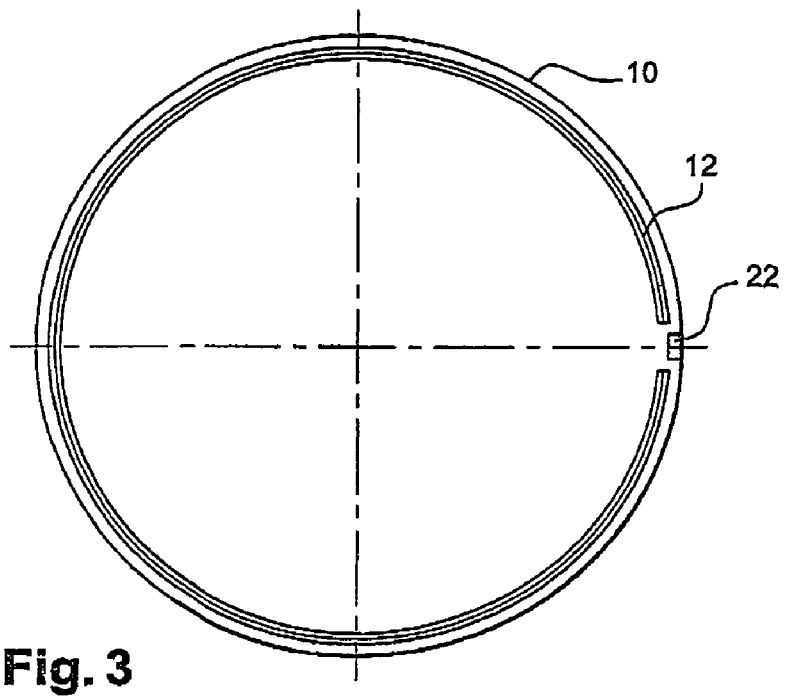
FIG. 3 depicts schematically a membrane comprising a weakened zone and a reinforcement zone according to a first embodiment of the invention.
Figure 4A:
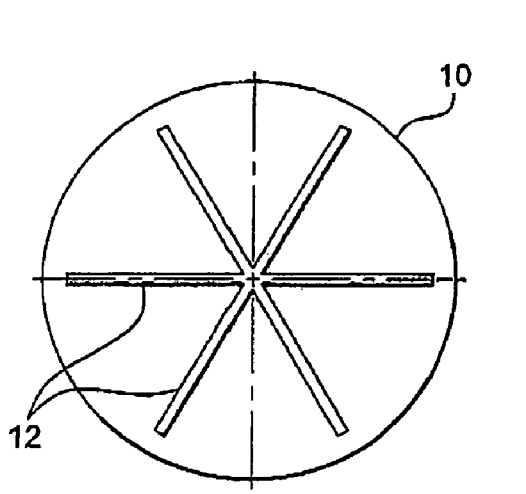
FIG. 4 depicts schematically variant membranes comprising a weakened zone.
Figure 4B:
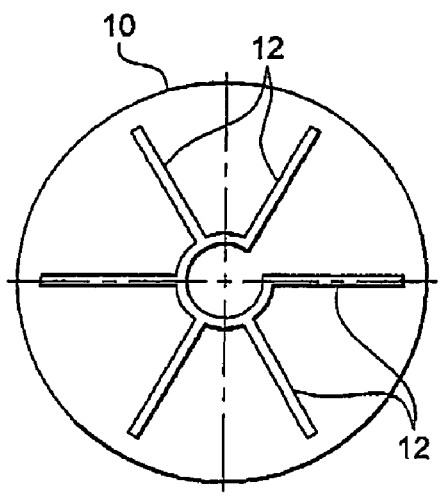

The membrane 10 preferably comprises one or more predetermined weakened zones 12 so as to facilitate its breaking, or even to cause the breaking thereof into a predetermined number of pieces. FIG. 3 shows such a membrane 10 according to a particular embodiment. The weakened zone 12 is intended to cause a separation of the membrane of the internal conduit of the luer connector 7 in a single piece. The membrane 10 also comprises a reinforcement zone 22 secured to the internal conduit so that this membrane 10 remains connected to the internal conduit 11 after separation. FIGS. 4a) and 4b) show variant membranes comprising weakened zones 12 allowing separation into several portions thereof.

The internal conduit 11 of the female luer connector 7 has a diameter $d_1$ less than the diameter d of the tube portion 6. In addition, the membrane 10 is preferably placed at a distance less than its diameter, which is substantially equal to $d_1$, from the opposite end of the female luer connector 7 so that at least some of the piece or pieces issuing from the separated membrane is forced out of the fluid passage.

The medical connector also comprises a locking member 13 intended to cooperate with a complementary locking member placed on a male luer connector in order to lock the male and female 7 luer connectors in the coupled position.

This locking member 13 comprises means of the non-return catch type. These means are for example inclined steps formed in a circle on the edge of a washer 23 coaxial with the tube portion 6 and female luer connector 7. This washer 23 is secured to the end of the tube portion 6.

The membrane 10 is advantageously designed so as to assist its injection during the manufacture of the connector. In addition, this membrane 10 does not generate any particles that could contaminate the medicinal solution. This result is obtained firstly by producing the membrane 10 with plastics material of low elasticity and secondly by providing very thin weakened zones 12, for example around a tenth of a millimeter.

Likewise, the geometry of the piercing element 3 has been designed so as to perforate the stopper of the bottle without generating fragments. This piercing element 3 has in particular few or no sharp edges.

The medical connector is produced from a plastics material preferably chosen from the group comprising polycarbonate or derivatives thereof, polyolefin (such as polyethylene, polypropylene, or a polypropylene copolymer) and polystyrene. It is preferably produced by moulding.

The invention also concerns a transfer set for preparing a mixture for medical purposes comprising a medical connector as described above.

Figure 5:
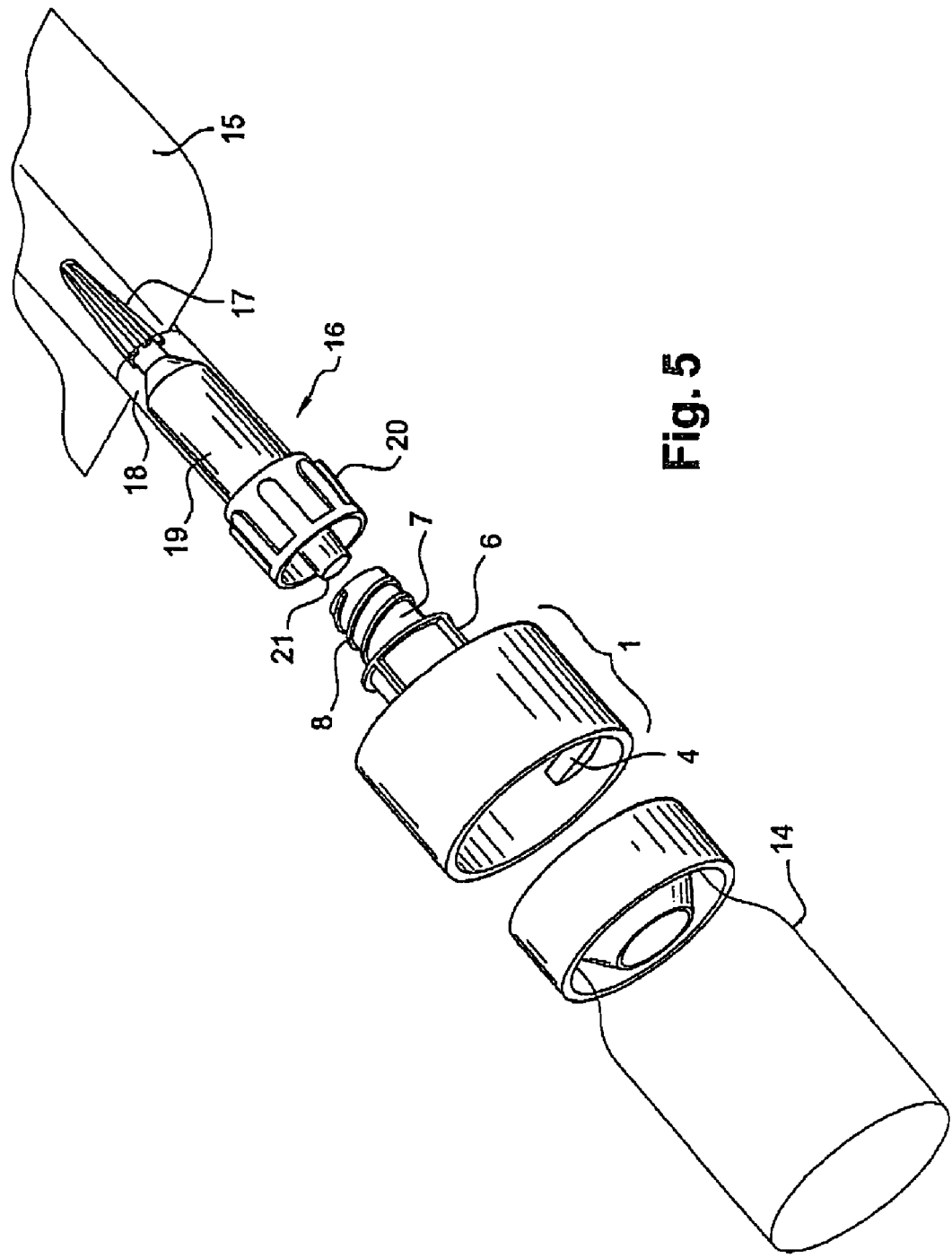
FIG. 5 shows schematically a transfer set according to a particular embodiment of the invention.

FIG. 5 shows such a transfer set according to one embodiment of the invention. The medical connector is identical to that described above and will consequently not be described further. This connector is intended to be connected to a bottle 14 containing an active substance that it is sought to mix with a liquid constituent such as a liquid to be diluted contained in a flexible pouch 15 in order to administer it to a patient.

The transfer set comprises a male luer connector 16. This male luer connector 16 comprises, at one end, a breakable section 17 engaged in the end of the tube 18 fixed to the flexible pouch 15. The male luer connector 16 comprises a cylindrical body 19 to which the breakable section 17 is attached in a known manner.

At its other end, the body 19 of the male luer connector 16 is extended by a cylindrical coupling ferrule 20 provided with a thread on the inside.

The body 16 is provided with a central conduit ending, on the breakable section 17 side, in the vicinity of a thin bridge where the separation between the breakable section 17 and the body 16 of the male luer connector 16 will take place, whereas at its other end the central conduit communicates with a coaxial tubular part 21 projecting slightly out of the ferrule 20. This tubular part 21 is also known by the term "perforator". Advantageously, the external wall of the tubular part 21 of the male luer connector 16 is also conical in order to facilitate the separation of the membrane 10.

As illustrated by FIG. 5, the male luer connector 16 is forcibly engaged in the end of the tube 18. The end of this tube can for example come into abutment against the ferrule 20, which has an outside diameter substantially greater than that of the main body 19 and corresponding substantially to that of the inside diameter of the tube 18.

The female luer connector 7 is able to engage in the ferrule 20 of the male luer connector 16, the tubular part 21, or perforator, then penetrating the internal conduit 18 of the female luer connector 7.

The thread 8 placed on the external surface of the body of the female luer connector 7 is intended to cooperate on the thread on the ferrule 20 so as to couple the male 16 and female 7 luer connectors by screwing.

The male luer connector 16 comprises a complementary locking member, opposite the locking member 13 of the female luer connector 7. This locking member comprises inclined steps complementary to those of the locking member of the female connector and provided in a circle on the edge of the ferrule 20.

These locking members 13 constitute a device of the catch type and cooperate so as at the end of screwing, to constitute a non-return latching preventing the unscrewing of the male 16 and female 7 luer connectors thus assembled.

The male luer connector is a single-piece connector obtained directly by moulding.

The invention claimed is:

1. A luer connector having an internal conduit (11) for a fluid to pass, comprising:
    an internal conduit (11) for fluid to pass;
    means (8) of connecting to a second luer connector (16), said second luer connector having a perforator (21), said connection means being placed at one end of said conduit (11),
    said one end also comprising a continuous rim (24) forming a projection in said conduit (11) so as to provide a seal on said conduit when said perforator is introduced into said conduit (11) with a view to coupling said connectors (7, 16), and
    an impervious breakable membrane (10) placed in said conduit (11) so as to be separated when said second luer connector (16) is coupled to said luer connector (7),
    wherein said membrane (10) comprises one or more predetermined weakened areas (12) on said membrane facilitating separation of a piece of the membrane from a remainder of the membrane,
    wherein said membrane comprises a reinforcement zone secured to said internal conduit, the reinforcement zone securing the piece of the membrane to the internal conduit upon the piece of the membrane being separated from the remainder of the membrane, and
    wherein said internal conduit (11) comprises a recess to accommodate the piece of the membrane separated from the remainder of the membrane.

2. A connector according to claim 1, where said membrane is made of a plastics material of low elasticity.

3. A connector according to claim 1, wherein said membrane is placed at a distance less than a diameter of the internal conduit, from the opposite end of the luer connector.

4. A connector according to claim 1, wherein said connection means (8) comprise a ferrule or external thread.

5. A connector according to claim 1, wherein said membrane (10) is placed in said conduit (11) so that a perforator (21) of said second connector covers a portion of the membrane (10) separated after coupling of said connectors (7, 16).

6. A connector according to claim 5, further comprising a locking member intended to cooperate with a complementary locking member placed on said second connector (16) in order to lock said luer connectors (7, 16) in the coupled position.

7. A connector according to claim 1, wherein said one end also comprises a breakable element (9).

8. A connector according to claim 7, wherein said breakable element (9) is a quarter-turn stopper.

9. A transfer set for preparing a mixture for medical purposes, comprising a luer connector according to claim 1 and a second luer connector (16) comprising at one end a perforator (21) and a complementary locking member for locking said luer connectors (7, 16) in the coupled position.

10. A transfer set according to claim 9, wherein said second luer connector (16) comprises at its end a breakable section (17) intended to be engaged in the end of a tube (18).

* * * * *